US012023085B2

United States Patent
Cowley

(10) Patent No.: US 12,023,085 B2
(45) Date of Patent: Jul. 2, 2024

(54) ULTRASONIC SYSTEMS AND METHODS WITH TISSUE RESISTANCE SENSING

(71) Applicant: Covidien LP, Mansfield, MA (US)

(72) Inventor: Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 343 days.

(21) Appl. No.: 16/999,264

(22) Filed: Aug. 21, 2020

(65) Prior Publication Data
US 2021/0059742 A1  Mar. 4, 2021

Related U.S. Application Data

(60) Provisional application No. 62/893,244, filed on Aug. 29, 2019.

(51) Int. Cl.
*A61B 18/14* (2006.01)
*A61B 18/00* (2006.01)
*A61B 18/12* (2006.01)

(52) U.S. Cl.
CPC ...... *A61B 18/1442* (2013.01); *A61B 18/1206* (2013.01); *A61B 2018/00077* (2013.01); *A61B 2018/00589* (2013.01); *A61B 2018/0063* (2013.01); *A61B 2018/00666* (2013.01); *A61B 2018/00702* (2013.01);
(Continued)

(58) Field of Classification Search
CPC ............ A61B 18/1442; A61B 18/1206; A61B 2018/00077; A61B 2018/00589; A61B 2018/0063; A61B 2018/00666; A61B 2018/00702; A61B 2018/00714; A61B 2018/0072; A61B 2018/00755;
(Continued)

(56) References Cited

U.S. PATENT DOCUMENTS 7,905,881 B2   3/2011  Masuda et al.
8,048,074 B2  11/2011  Masuda
(Continued)

FOREIGN PATENT DOCUMENTS

JP   2018519918 A   7/2018
WO  2010084684 A1   7/2010
WO  2017003854 A2   1/2017

OTHER PUBLICATIONS

Extended European Search Report issued in corresponding European Application No. EP 20193127.6 dated Mar. 30, 2021, 9 pages.
(Continued)

*Primary Examiner* — Linda C Dvorak
*Assistant Examiner* — Abigail Bock
(74) *Attorney, Agent, or Firm* — Carter, DeLuca & Farrell LLP

(57) ABSTRACT

Surgical systems include an ultrasonic device, a generator coupled to the ultrasonic device, and a return pad. The generator is configured to control supply of the ultrasonic energy to the ultrasonic device and control supply of an energy pulse to the ultrasonic device at different times. The ultrasonic device generates a current pulse signal in response to the energy pulse. The generator also measures a current feedback signal at the return pad, the current feedback signal resulting from the current pulse signal, and estimate a tissue property of tissue grasped by the ultrasonic device based on the current feedback signal.

17 Claims, 5 Drawing Sheets

(52) U.S. Cl.
CPC ............... *A61B 2018/00714* (2013.01); *A61B 2018/0072* (2013.01); *A61B 2018/00755* (2013.01); *A61B 2018/00898* (2013.01); *A61B 2018/00922* (2013.01); *A61B 2018/00994* (2013.01); *A61B 2018/1412* (2013.01)

(58) Field of Classification Search
CPC .......... A61B 2018/00898; A61B 2018/00922; A61B 2018/00994; A61B 2018/1412
See application file for complete search history.

(56) References Cited

U.S. PATENT DOCUMENTS

| | | | |
|---|---|---|---|
| 8,652,132 B2 | 2/2014 | Tsuchiya et al. | |
| 8,663,223 B2 | 3/2014 | Masuda et al. | |
| 8,808,204 B2 | 8/2014 | Irisawa et al. | |
| 8,814,855 B2 * | 8/2014 | DiCarlo | A61B 18/14 606/41 |
| 9,039,690 B2 | 5/2015 | Kersten et al. | |
| 9,326,787 B2 | 5/2016 | Sanai et al. | |
| 9,681,912 B2 | 6/2017 | Tsubuku et al. | |
| 9,801,649 B2 | 10/2017 | Akagane et al. | |
| 9,808,305 B2 | 11/2017 | Hareyama et al. | |
| 9,833,280 B2 * | 12/2017 | Hirai | A61B 18/1445 |
| 9,872,726 B2 | 1/2018 | Morisaki | |
| 9,901,754 B2 | 2/2018 | Yamada | |
| 9,949,785 B2 | 4/2018 | Price et al. | |
| 10,045,815 B2 | 8/2018 | Tsubuku | |
| 10,172,671 B2 | 1/2019 | Masuda et al. | |
| 10,470,791 B2 | 11/2019 | Houser | |
| 10,575,895 B2 | 3/2020 | Shelton, IV et al. | |
| 10,660,692 B2 | 5/2020 | Lesko et al. | |
| 10,688,321 B2 | 6/2020 | Wiener et al. | |
| 2002/0183774 A1 | 12/2002 | Witt et al. | |
| 2008/0249523 A1 | 10/2008 | McPherson et al. | |
| 2011/0112530 A1 | 5/2011 | Keller | |
| 2013/0267975 A1 | 10/2013 | Timm et al. | |
| 2015/0088117 A1 | 3/2015 | Gilbert et al. | |
| 2017/0000541 A1 | 1/2017 | Yates et al. | |
| 2017/0000542 A1 | 1/2017 | Yates et al. | |
| 2017/0000553 A1 | 1/2017 | Wiener et al. | |
| 2017/0000554 A1 | 1/2017 | Yates et al. | |
| 2017/0086908 A1 * | 3/2017 | Wiener | A61B 18/1206 |
| 2017/0164972 A1 | 6/2017 | Johnson et al. | |
| 2017/0164997 A1 | 6/2017 | Johnson et al. | |
| 2017/0202598 A1 * | 7/2017 | Shelton, IV | H01M 50/267 |
| 2017/0202605 A1 * | 7/2017 | Shelton, IV | A61B 18/1447 |
| 2017/0325874 A1 | 11/2017 | Noack et al. | |
| 2018/0206905 A1 * | 7/2018 | Batchelor | A61B 18/14 |
| 2018/0318000 A1 | 11/2018 | Honda et al. | |
| 2018/0333177 A1 | 11/2018 | Leuck et al. | |
| 2018/0333181 A1 | 11/2018 | Lesko et al. | |
| 2018/0333182 A1 | 11/2018 | Clauda | |
| 2018/0333185 A1 | 11/2018 | Asher et al. | |
| 2018/0333187 A1 | 11/2018 | Sawhney | |
| 2018/0333188 A1 | 11/2018 | Nott et al. | |
| 2018/0333189 A1 | 11/2018 | Asher et al. | |
| 2018/0333190 A1 | 11/2018 | Krumm et al. | |
| 2019/0142489 A1 | 5/2019 | Hayashida et al. | |
| 2019/0201074 A1 | 7/2019 | Yates et al. | |
| 2019/0201076 A1 | 7/2019 | Honda et al. | |
| 2019/0336202 A1 | 11/2019 | Kobayashi et al. | |
| 2020/0222111 A1 | 7/2020 | Yates et al. | |

OTHER PUBLICATIONS

European Communication Pursuant to Article 94(3) EPC issued in corresponding European Application No. 20 193 127.6 dated Jan. 31, 2023, 5 pages.

Japanese Office Action issued in corresponding Japanese Application No. 2020-144169 dated Mar. 29, 2024, 11 pages.

* cited by examiner

ULTRASONIC SYSTEMS AND METHODS WITH TISSUE RESISTANCE SENSING

CROSS-REFERENCE TO RELATED APPLICATIONS

This application claims the benefit of and priority to U.S. Provisional Patent Application Ser. No. 62/893,244 filed Aug. 29, 2019, the entire disclosure of which is incorporated by reference herein.

FIELD

The present disclosure is generally related to surgical systems and methods, and more particularly, to systems that apply ultrasonic energy and control the application of ultrasonic energy based on a sensed tissue property, such as tissue resistance.

BACKGROUND

Ultrasonic surgical instruments employ ultrasonic energy transmitted along a waveguide to an end effector of the ultrasonic surgical instrument to treat tissue with the ultrasonic energy. Ultrasonic surgical instruments utilize both mechanical clamping action and energy to treat tissue, including, for example, coagulate, cauterize, and/or seal tissue. There is continued interest in improving the capabilities and effectiveness of ultrasonic surgical instruments to treat tissue.

SUMMARY

In one aspect, the present disclosure provides a surgical system that includes: an ultrasonic device having a first jaw member and a second jaw member; a return electrode; and a generator coupled to the ultrasonic device and the return electrode. The ultrasonic device is configured receive ultrasonic energy and to treat tissue grasped between the first jaw member and the second jaw member. The generator is configured to: control supply of the ultrasonic energy to the ultrasonic device at a first time; control supply of an energy pulse to the ultrasonic device at a second time, different from the first time; measure a current feedback signal at the return electrode resulting from a current pulse signal generated by the ultrasonic device in response; and estimate a tissue property of the tissue grasped between the first jaw member and the second jaw member based on the current feedback signal.

In aspects, the generator is configured to control the ultrasonic energy to heat the tissue to a predetermined temperature for a period of time until the tissue is sealed.

In aspects, the generator estimates a change in tissue impedance.

In aspects, the generator may be further configured to determine desiccation or coagulation of the tissue based on the change in tissue impedance.

In aspects, the generator may be further configured to provide an audio tone when the change in tissue impedance reaches a threshold value.

In aspects, the generator may be configured to periodically switch between supplying the ultrasonic energy and supplying the energy pulse.

In accordance with another aspect of the disclosure, a method for controlling energy provided to an ultrasonic device of an ultrasonic system. The method includes: controlling supply of an energy pulse to the ultrasonic device at a first time to establish a tissue property baseline; controlling supply of ultrasonic energy to the ultrasonic device at a second time; controlling supply of the energy pulse to the ultrasonic device at a third time different from the first time; after the each energy pulse is supplied, measuring a current feedback signal at a return electrode of the surgical system resulting from the current pulse signal generated by the ultrasonic device in response to the energy pulse; and estimating a tissue property of tissue grasped between first and second jaw members of the ultrasonic device based on the current feedback signal.

In aspects, treating the tissue includes sealing the tissue by heating the tissue to a predetermined temperature, and maintaining the temperature for a period of time while the ultrasonic device compresses the tissue.

In aspects, the tissue property estimated may be a change in tissue impedance.

In aspects, the method includes determining desiccation or coagulation of the tissue based on the change in tissue impedance.

In aspects, the method includes providing an audio tone when the change in tissue impedance reaches the threshold value.

In aspects, controlling the supply of ultrasonic energy and the energy pulse includes periodically switching between supplying the ultrasonic energy and supplying the energy pulse.

In accordance with another aspect of the disclosure, a surgical instrument includes: a housing; a shaft extending distally from the housing; a transducer configured to receive ultrasonic energy; an ultrasonic waveguide coupled with the transducer and extending through the shaft; a conductor configured to convey a current pulse; and an end effector assembly supported at a distal end portion of the shaft and coupled to the ultrasonic waveguide. The transducer provides ultrasonic motion based on the ultrasonic energy. The end effector assembly has a first jaw member having an electrically-conductive tissue-contacting surface connected to the conductor, and a second jaw member positioned opposite the first jaw member. At least one of the first jaw member or the second jaw member includes a blade acoustically coupled to the ultrasonic waveguide. The surgical instrument also includes a controller configured to apply the current pulse through the conductor and apply the ultrasonic energy to the transducer at different times.

In aspects, in treating the tissue by ultrasonic motion, the blade heats the tissue to a predetermined temperature, and maintains the temperature for a period of time, and the end effector assembly applies clamping force to compress the tissue until the tissue is sealed.

In aspects, the electrically-conductive tissue-contacting surface of the first jaw member is adapted to apply the current pulse signal to the tissue grasped between the first jaw member and the second jaw member.

In aspects, the controller applies the current pulse and applies the ultrasonic energy at different times by periodically switching between applying the current pulse to through the conductor and applying the ultrasonic energy to the transducer during sealing.

In accordance with another aspect of the disclosure, a surgical instrument includes: a handle assembly; a shaft extending distally from the handle assembly; a transducer configured to receive ultrasonic energy; an ultrasonic waveguide coupled with the transducer and extending through the shaft; a conductor path configured to convey a current pulse; an end effector assembly supported at a distal end portion of the shaft and coupled to the ultrasonic waveguide; and a controller configured to apply the current pulse through the conductor path and apply the ultrasonic energy to the transducer at different times. The end effector has a jaw member having an electrically-conductive tissue-contacting surface connected to the conductor path, and a blade connected to the conductor path and positioned opposite the first jaw member. The blade is acoustically coupled to the ultrasonic waveguide.

In aspects, the electrically-conductive tissue-contacting surface of at least one of the jaw member or the blade may be adapted to apply the current pulse to the tissue grasped between the jaw member and the blade.

In aspects, the controller applies the current pulse and applies the ultrasonic energy at different times by periodically switching between applying the current pulse through the conductor and applying the ultrasonic energy to the transducer during sealing.

In accordance with another aspect of the disclosure, a surgical instrument includes: an ultrasonic device including a jaw member and a blade each having an electrically-conductive tissue-contacting surface, the ultrasonic device configured to receive ultrasonic energy and to treat tissue grasped between the jaw member and the blade; and a generator coupled to the ultrasonic device. The generator is configured to control supply of the ultrasonic energy to the ultrasonic device at a first time; control supply of an energy pulse to the ultrasonic device at a second time different from the first time; measure a current feedback signal at a return electrode coupled to at least one of the jaw member or the blade, the feedback signal resulting from a current pulse signal generated by the ultrasonic device in response to the energy pulse; and estimate a tissue property of the tissue grasped between the jaw member and the blade based on the current feedback signal.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Particular embodiments of the disclosure are described hereinbelow with reference to the accompanying drawings. In the following description, well-known functions or constructions are not described in detail to avoid obscuring the present disclosure in unnecessary detail. As used herein, the term "distal" refers to that portion which is farther from the user while the term "proximal" refers to that portion which is closer to the user or surgeon.

The following aspects of ultrasonic surgical systems and methods include an ultrasonic device for treating tissue and incorporate features to provide indication of proper and sufficient tissue desiccation and/or coagulation.

The systems and methods of the disclosure detailed below may be incorporated into surgical systems of different types or configurations and may be employed to perform a variety of surgical procedures. The particular illustrations and embodiments disclosed herein are merely exemplary and do not limit the scope or applicability of the disclosed technology.

Figure 1:
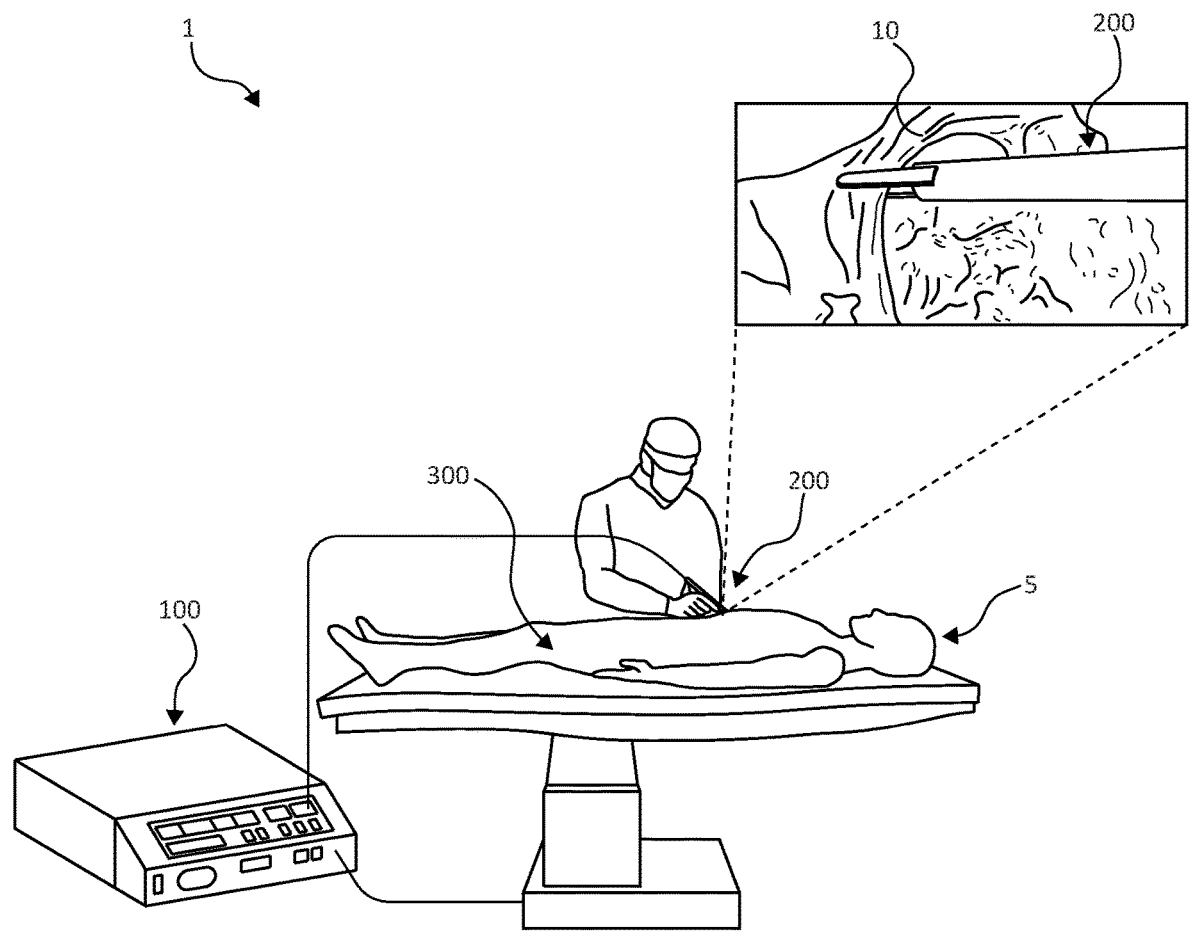
FIG. 1 is a diagram of a system for sensing tissue resistance according to aspects of the disclosure.

FIG. 1 illustrates a surgical system 1 according to aspects of the disclosure. Surgical system 1 includes an ultrasonic energy source, such as, for example, a generator 100, a surgical instrument 200, and a return electrode, such as, for example a return pad 300. Surgical instrument 200 and return pad 300 are coupled to generator 100. Although generator 100 is illustrated as delivering ultrasonic energy to a separate surgical instrument 200, this is by example only and should not be construed as limiting. Generator 100 in various embodiments may be integral with the surgical instrument 200, such as an instrument described in U.S. Patent Application Publication No. 2016/0374711, which is hereby incorporated by reference herein in its entirety.

Figure 2:
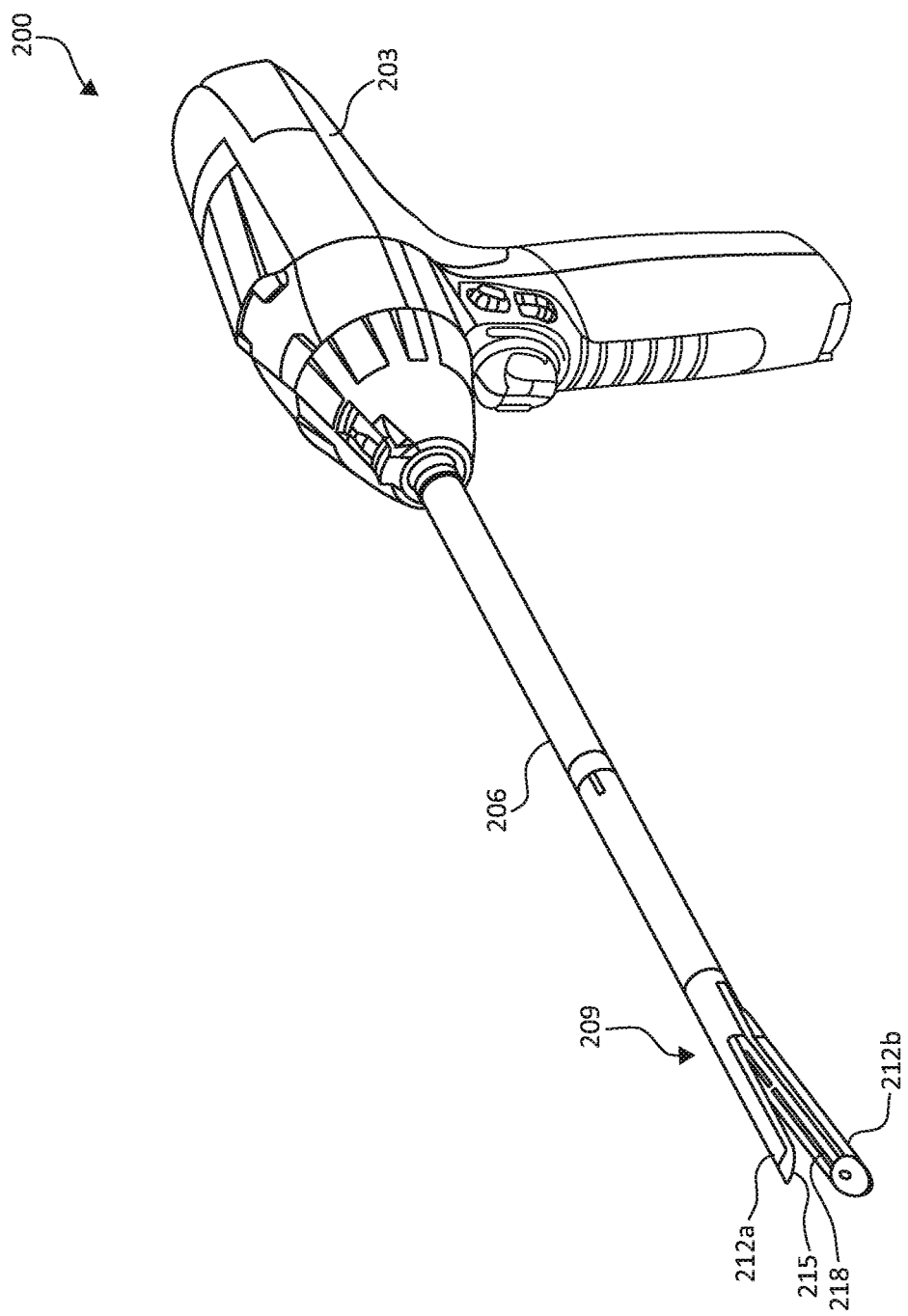
FIG. 2 is a diagram of a surgical instrument according to aspects of the disclosure.

FIG. 2 illustrates surgical instrument 200 of surgical system 1 according to aspects of the disclosure. Surgical instrument 200 includes a housing 203, an outer shaft 206, a conductor (not shown), and a waveguide (not shown) extending through outer shaft 206, and an end effector assembly 209. The waveguide extends distally from housing 203 through outer shaft 206.

End effector assembly 209 is supported at a distal end portion of outer shaft 206. End effector assembly 209 is coupled to the waveguide and to the conductor and generally includes a first jaw member 212a having an electrically-conductive tissue-contacting surface 215 adapted to connect to generator 100 via the conductor, and a second jaw member 212b oppositely disposed to first jaw member 212a. In embodiments, the electrically-conductive tissue-contacting surface of first jaw member 212a is an active electrode that provides electrical current, and second jaw member 212b does not include any active electrode or any return electrode. In embodiments, the electrically-conductive tissue-contacting surface and the active electrode are located in second jaw member 212b, and first jaw member 212a does not include any active electrode or any return electrode. In embodiments, the active electrode may be located at another tissue contacting surface of end effector assembly 209 that is not on first jaw member 212a or second jaw member 212b. In embodiments, end effector assembly 209 does not include any return electrode. Accordingly, end effector assembly 209 can provide electrical current using an active electrode, but end effector 209 may not receive any return current because it does not include any return electrode.

First jaw member 212a or second jaw member 212b may further include a blade 218 acoustically coupled to the waveguide. First jaw member 212a is movable relative to second jaw member 212b, or vice versa, between a spaced-apart position and an approximated position to grasp tissue 10 of patient 5 therebetween. As persons skilled in the art will understand, ultrasonic movement is conveyed to the waveguide of surgical instrument 200, and to blade 218, while the first and second jaw members grasp tissue 10 in the approximated position. The ultrasonic movement is provided by a transducer (not shown) that is driven by ultrasonic electrical energy supplied by generator 100. The ultrasonic motion of blade 218 heats the tissue 10, thereby allowing surgical instrument 200 to coagulate, desiccate, and/or otherwise treat tissue. In embodiments, the ultrasonic energy can be provided by a generator that is separate from the surgical instrument 200, as shown in FIG. 1. In other embodiments, the ultrasonic energy can be provided by a generator 100 that is internal to surgical instrument 200.

In accordance with aspects of the present disclosure, generator 100 can supply an energy pulse to surgical instrument 200, which uses the energy pulse to generate a current pulse through the conductor to the electrically-conductive tissue-contacting surface 215 of first jaw member 212a. The current pulse can be applied to tissue 10 grasped between first jaw member 212a and second jaw member 212b. In embodiments, the energy pulse can be provided by a generator 100 that is separate from the surgical instrument 200, as shown in FIG. 1. In other embodiments, the energy pulse can be provided by a generator 100 that is internal to the surgical instrument 200. In yet other embodiments, ultrasonic energy can be provided by a generator 100 that is separate from surgical instrument 200, while the energy pulse can be provided by a generator 100 that is internal to surgical instrument 200. In yet other embodiments, ultrasonic energy can be provided by a generator 100 that is internal to surgical instrument 200, while the energy pulse can be provided by a generator 100 that is separate from surgical instrument 200. Surgical instrument 200 further includes a controller (not shown) configured to receive and apply the energy pulse via the conductor and apply the ultrasonic energy via the transducer/waveguide, at different times.

End effector assembly 209 does not include any return electrode. With reference again to FIG. 1, return pad 300 is configured to adhere externally to patient 5. Return pad 300 forms part of an electrical loop that includes generator 100, surgical instrument 200, patient 5, and return pad 300. Generator 100 supplies the energy pulse to surgical instrument 200, which provides a current pulse to patient 5 via tissue 10 grasped between first jaw member 212a and second jaw member 212b of surgical instrument 200. The current pulse applied to tissue 10 of patient 5 travels through tissue 10 to return pad 300, which is coupled to generator 100 through a return terminal of generator 100. Although return pad 300 is described herein as a "pad," this is by example only and should not be construed as limiting. Return pad 300, in various embodiments, may be a grounding pad, bovie pad, neutral electrode, patient plate, and/or the like. In various embodiments, in lieu of return pad 300, for example the return electrode is located in the first jaw member 212a or the second jaw member 212b which is configured to provide the energy pulse, such as, for example, a single jaw having two isolated electrodes arranged side by side or front to back. One example of such a configuration will be discussed later herein in connection with FIG. 5.

The electrical loop enables the generator 100 to determine or estimate various tissue properties. Various aspects of using a return pad to measure a feedback signal for determining or estimating tissue property are described in U.S. Pat. No. 5,776,130, which is hereby incorporated by reference herein in its entirety. For example, the tissue property determined or estimated by generator 100 can be the impedance of the tissue between surgical instrument 200 and return pad 300. In embodiments, generator 100 is separate from surgical instrument 200 and return pad 300 is connected to a return terminal of generator 100, as shown in FIG. 1. In other embodiments, generator 100 is internal to surgical instrument 200, and return pad 300 is connected to a return terminal of surgical instrument 200.

Accordingly, generator 100 employed in the present surgical systems may provide both ultrasonic energy and energy pulses. The ultrasonic energy is used by surgical instrument 200 to apply mechanical motion to treat patient tissue. The energy pulse is used by surgical instrument 200 to apply an electrical current to patient tissue to estimate a tissue property, such as tissue impedance.

Generator 100 is configured to control supply of the ultrasonic energy to surgical instrument 200. During supply of the ultrasonic energy to surgical instrument 200, end effector 209 heats up tissue 10 grasped between first jaw member 212a and second jaw member 212b. Tissue 10 can be heated to a predetermined temperature without compromising the surrounding tissue. When the predetermined temperature is achieved, it can be maintained for a period of time while clamping force is applied to tissue 10 grasped between first jaw member 212a and second jaw member 212b of surgical instrument 200. The combination of temperature and clamping force operate to compress and seal tissue 10. Once tissue 10 is properly sealed, tissue 10 can be dissected. Aspects of determining or estimating temperature are described in U.S. Pat. No. 5,776,130, which was previously incorporated by reference herein. In various embodiments, jaw force is applied to the tissue to detect a predetermined temperature based on the tissue tension against the waveguide.

Generator 100 is configured to determine if a proper seal has been achieved by surgical instrument 200. Generator 100 controls supply of the energy pulse to surgical instrument 200, which is configured to generate a current pulse signal based on the energy pulse. Generator 100 measures a current feedback signal at return pad 300, resulting from the current pulse signal generated. Generator 100 determines or estimates a tissue property of tissue 10 grasped between first jaw member 212a and second jaw member 212b based on the current feedback signal. In embodiments, generator 100 determines or estimates if tissue 10 has been properly sealed based on the tissue property by measuring a change in tissue impedance. In embodiments, generator 100 is configured to provide an audio tone if the change in tissue impedance achieves a predetermined threshold value.

In accordance with aspects of the present disclosure, generator 100 controls the generation of ultrasonic energy and the energy pulse so that they are supplied at different times. In embodiments, generator 100 periodically switches from supplying ultrasonic energy to supplying energy pulse. In embodiments, generator 100 may simultaneously supply ultrasonic energy and energy pulse.

Figure 3:
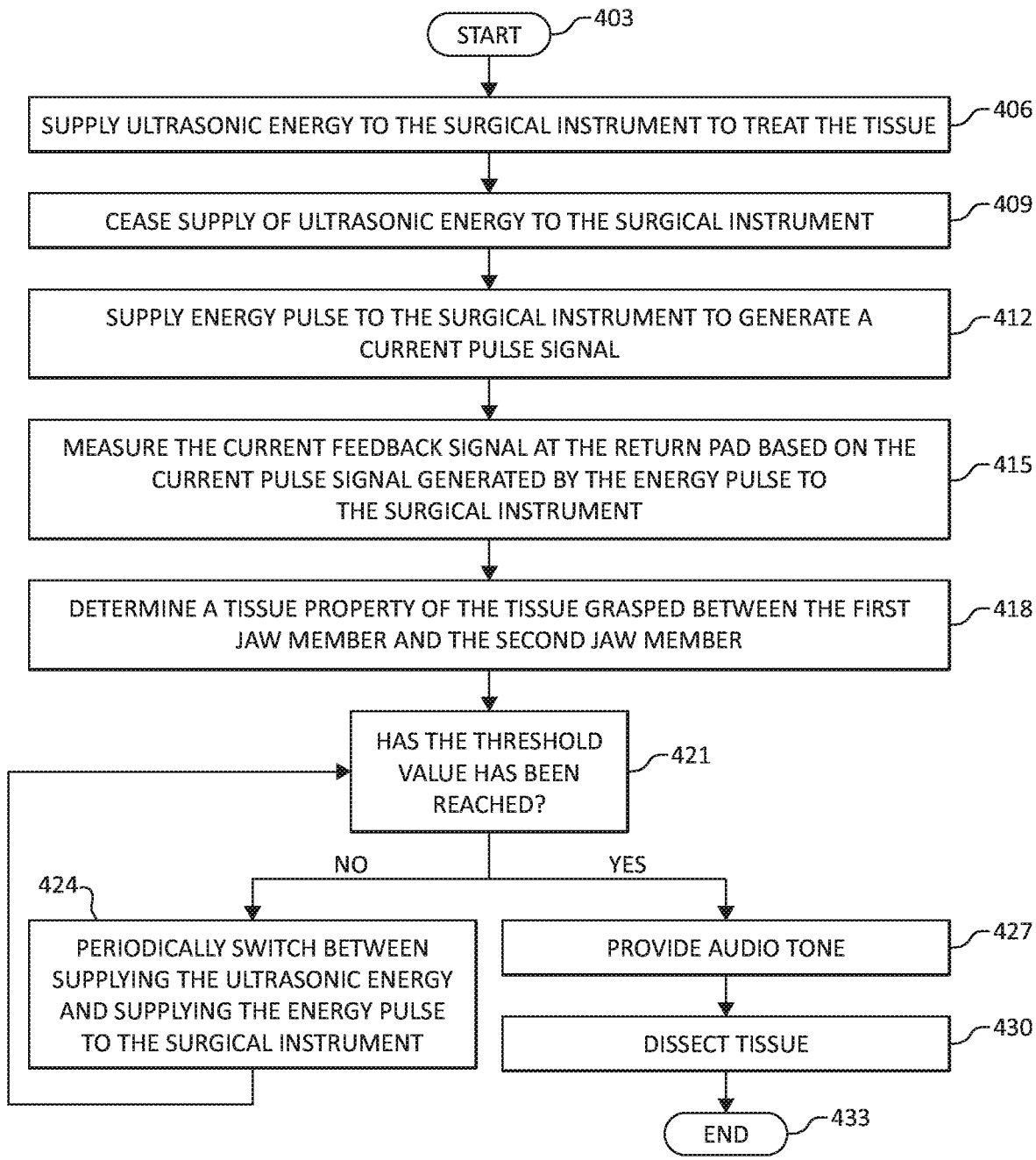
FIG. 3 is a flow chart illustrating an example of a procedure for sensing the tissue resistance according to aspects of the disclosure.

FIG. 3 illustrates a flow chart of an illustrative method of operating a surgical system in accordance with the present disclosure. At the start of the operation 401, and with reference also to FIGS. 1 and 2, tissue 10 is grasped between first jaw member 212a and second jaw member 212b. At step 403, prior to treatment of tissue 10, generator 100 supplies an energy pulse to surgical instrument 200, and surgical instrument 200 generates a current pulse signal based on the energy pulse. The current pulse signal is applied to tissue 10 grasped between first jaw member 212a and second jaw member 212b and travels through patient 5 to return pad 300. An initial tissue impedance is measured based on the current feedback signal returned to generator 100 via return pad 300. At step 406, generator 100 supplies ultrasonic energy to surgical instrument 200, which is configured to treat tissue 10 by ultrasonic motion within first jaw member 212a and/or second jaw member 212b. The ultrasonic energy enables surgical instrument 200 to generate ultrasonic motion, which heats up tissue 10. In embodiments, generator 100 can supply the ultrasonic energy for a predetermined period of time. At step 409, generator 100 ceases supply of ultrasonic energy to surgical instrument 200.

At step 412, generator 100 supplies an energy pulse to surgical instrument 200, and surgical instrument 200 generates a current pulse signal based on the energy pulse. The current pulse signal is applied to tissue 10 grasped between first jaw member 212*a* and second jaw member 212*b* and travels through patient 5 to return pad 300. At step 415, generator 100 measures the current feedback signal returned to generator 100 via return pad 300. At step 418, generator 100 determines or estimates a tissue property of tissue 10 grasped between first jaw member 212*a* and second jaw member 212*b* based on the current feedback signal. At step 421, generator 100 determines or estimates the tissue property by measuring the change in tissue impedance from the initial tissue impedance until a threshold value is reached.

At step 427, if the threshold value has been reached, generator 100 provides an audio tone to indicate that tissue 10 is sealed and ready for dissection. At step 430, surgical instrument 200 may dissect tissue 10. At step 424, if the threshold value has not been reached, generator 100 switches back to supplying ultrasonic energy to surgical instrument 200 to continue treatment of tissue 10, and returns to step 406. In this manner, generator 100 periodically switches between supplying ultrasonic energy and supplying energy pulses to surgical instrument 200 until the threshold value has been reached.

The operation of FIG. 3 is exemplary and variations are contemplated to be within the scope of the present disclosure. For example, in embodiments, step 424 may occur before step 421. For example, generator 100 may switch to supplying ultrasonic energy while it determines whether the threshold value has been reached. If so, the operation can proceed to step 427. If not, the operation can return to step 406. As an additional variation, step 421 can estimate whether a seal has been achieved in other ways than as described herein. Accordingly, the manner of estimating whether a seal has been achieved is not limited to the exemplary technique disclosed herein. Other variations are contemplated to be within the scope of the present disclosure.

Figure 4:
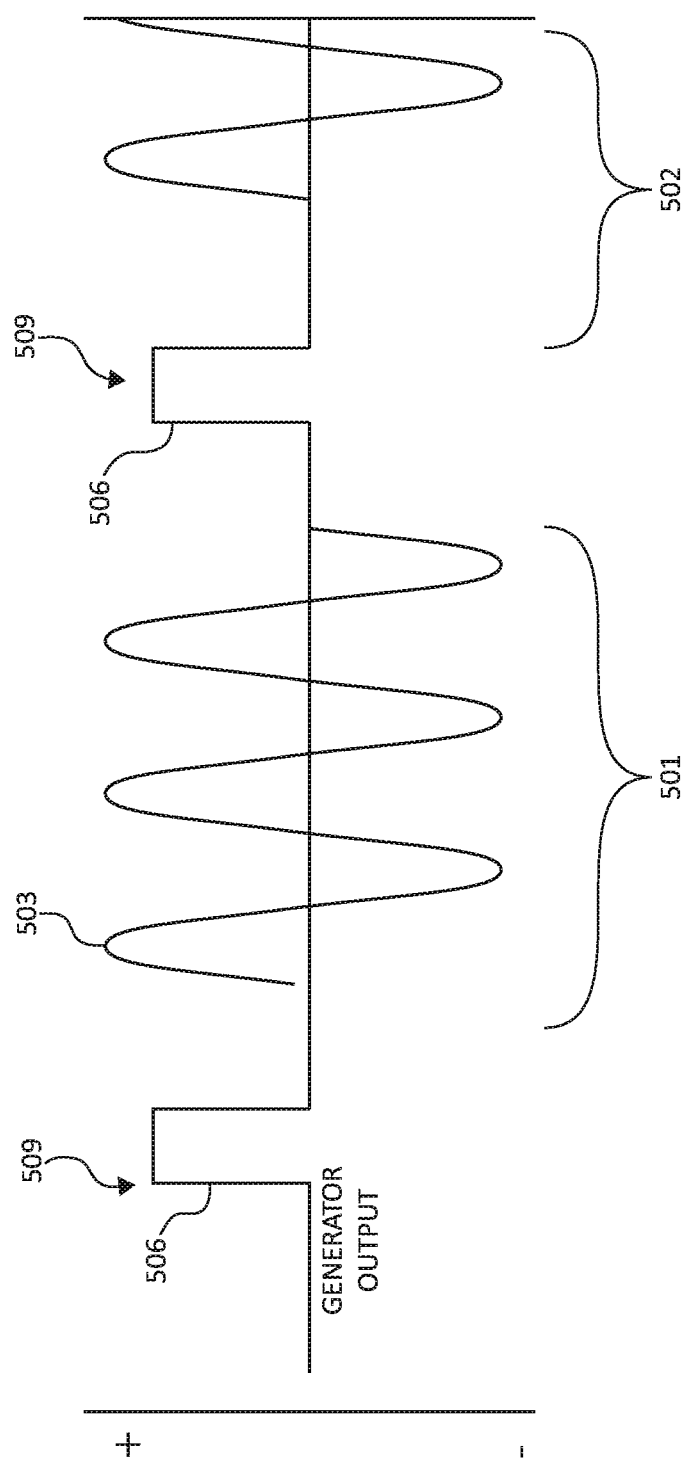
FIG. 4 is a diagram of energy provided by a generator, including switching between ultrasonic energy and energy pulse according to aspects of the disclosure.

FIG. 4 illustrates an exemplary energy signal supplied by a generator. The energy signal periodically switches between supplying ultrasonic energy 503 to surgical instrument 200 and supplying energy pulse 506 to surgical instrument 200 during sealing. Prior to treatment, energy pulse 506 is supplied by generator 100 to determine an initial tissue impedance based on the current feedback signal returned, and then generator 100 ceases supply of energy pulse 506. Ultrasonic energy 503 is supplied by generator 100 for a first period of time 501, and then generator 100 ceases supply of ultrasonic energy 503 and switches to supplying energy pulse 506 for a period of time 509. In embodiments, period of time 501, period of time 509, energy pulse 506 is supplied may vary. After, energy pulse 506 is supplied, the current feedback signal can be measured. If generator 100 determines that the threshold value has not been reached, generator 100 switches back to supplying ultrasonic energy 503 to surgical instrument 200 for a second period of time 502. The controller of surgical instrument 200 may further adjust second time period 502, by extending or shortening the duration, based on the measured change in tissue impedance from the initial tissue impedance. In particular, for example, the closer the change in tissue impedance is from the threshold value, second period of time 502 is shortened and the further the change in tissue impedance is from the threshold value, second period of time 502 is extended. In embodiments, generator 100 may switch to supplying ultrasonic energy while it determines whether a threshold value has been reached. In embodiments, in the case where generator 100 simultaneously supplies ultrasonic energy and energy pulse, continuous measurement of the change in tissue impedance may be achieved and is contemplated. The energy waveform of FIG. 4 is illustrative and does not limit the types of energy waveforms that are applicable to the operations disclosed herein.

Figure 5:
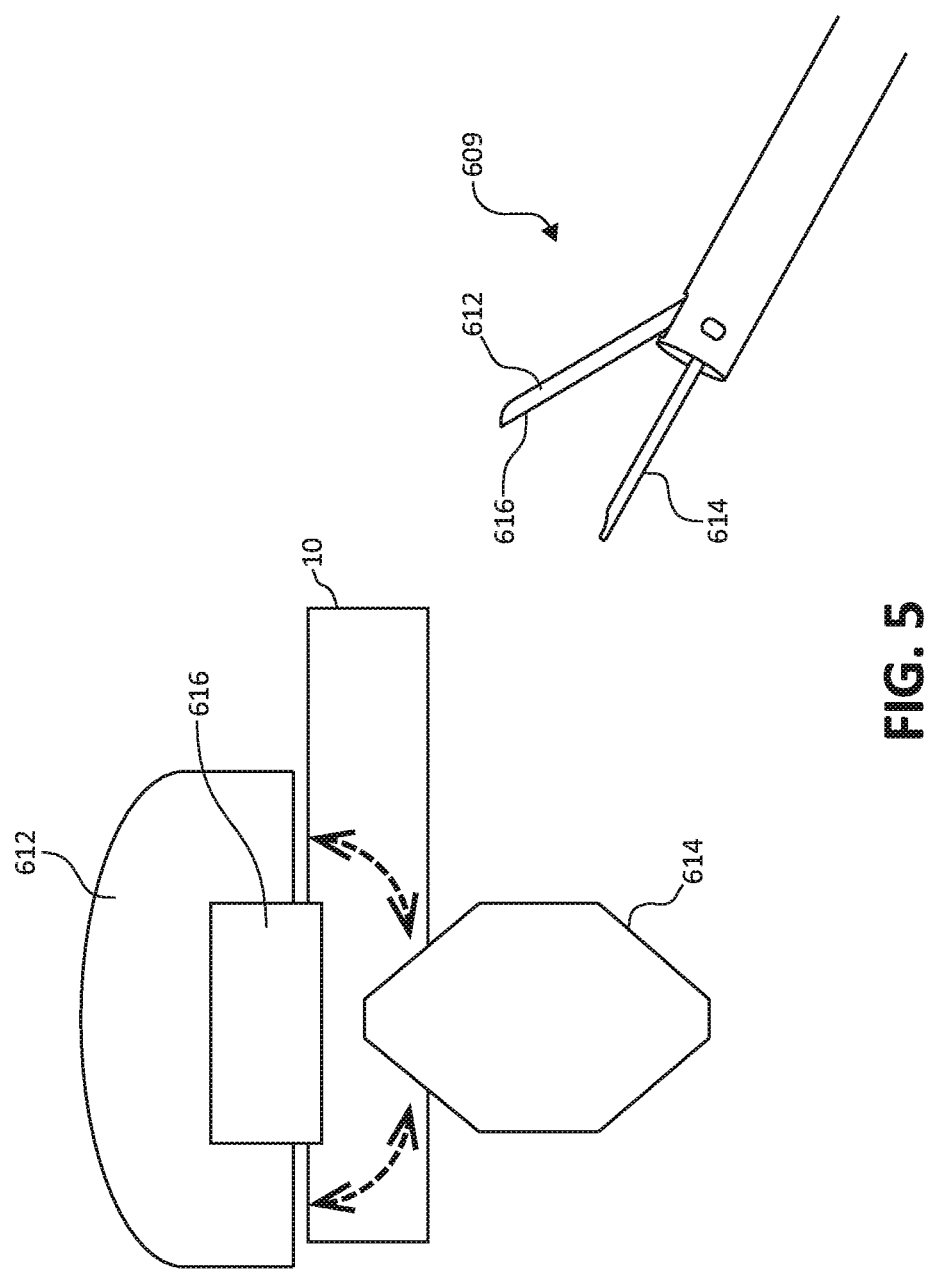
FIG. 5 is a diagram of an exemplary surgical instrument with a return electrode in an end effector, provided in accordance with aspects of present disclosure.

FIG. 5 illustrates another embodiment of surgical system 1, which is similar to the electrical loop of FIG. 1 without a return pad. In the illustrative embodiment of FIG. 5, the generator and the surgical instrument form a conductor path without a return pad. End effector assembly 609 of surgical instrument 600 includes a jaw member 612 and a blade 614. Jaw member 612 includes a jaw liner 616 fabricated from a compliant material that allows blade 614 to vibrate while in contact therewith without causing damage to blade 614 or other components of surgical instrument 600, and without compromising the hold on tissue grasped therebetween. Jaw liner 616 is configured to be situated in support base (not shown) such that blade 614 makes contact with jaw liner 616 rather than support base (not shown) when end effector assembly 609 is in the clamped condition.

Both jaw member 612 and blade 614 are configured to be an electrically-conductive tissue-contacting surface, which are electrically isolated from one another. In embodiments, the electrically-conductive tissue-contacting surface of jaw member 612 is an active electrode that provides electrical current, and blade 614 is a return electrode. In embodiments, the electrically-conductive tissue-contacting surface of blade 614 is an active electrode that provides electrical current, and jaw member 612 is a return electrode. As described above, the electrical loop enables the generator 100 to determine or estimate various tissue properties. In operation, generator 100 supplies the energy pulse to surgical instrument 600, which provides a current pulse to patient 5 via tissue 10 grasped between jaw member 612 and blade 614 of surgical instrument 600. The current pulse applied to tissue 10 of patient 5 travels through tissue 10 from either jaw member 612 or blade 614 to return electrode of the opposing jaw member 612 or blade 614, which is coupled to generator 100 through a return terminal of generator 100.

The embodiment of FIG. 5 is exemplary, and variations are contemplated to be within the scope of the present disclosure. For example, in embodiments, the active electrode may be located at another tissue contacting surface of end effector assembly 609 that is not on jaw member 612 or blade 614. In embodiments, end effector assembly 609 does not include any return electrode. Accordingly, end effector assembly 609 can provide electrical current using an active electrode, but end effector 609 may not receive any return current because it does not include any return electrode. Other variations are contemplated to be within the scope of the present disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The above description should not be construed as limiting, but merely as exemplifications of embodiments. Those skilled in the art will envision other modifications within the scope and spirit of the present disclosure.

What is claimed is:

1. A surgical system, comprising:
   an ultrasonic device including a first jaw member and a second jaw member, the ultrasonic device configured to receive ultrasonic energy and to treat tissue grasped between the first jaw member and the second jaw member;
   a return electrode remote from the ultrasonic device; and
   a generator coupled to the ultrasonic device and the return electrode, the generator configured to:
      control supply of an initial energy pulse to the ultrasonic device at an initial time;
      measure an initial current feedback signal at the return electrode resulting from an initial current pulse signal generated by the ultrasonic device in response to the initial energy pulse;
      estimate an initial tissue property value of the tissue grasped between the first jaw member and the second jaw member based on the initial current feedback signal;
      control supply of the ultrasonic energy to the ultrasonic device at a first time after the initial time;
      control supply of a subsequent energy pulse to the ultrasonic device at a subsequent time after the first time;
      measure a subsequent current feedback signal at the return electrode resulting from a subsequent current pulse signal generated by the ultrasonic device in response to the subsequent energy pulse;
      estimate a subsequent tissue property value of the tissue grasped between the first jaw member and the second jaw member based on the subsequent current feedback signal;
      compare the initial tissue property value with the subsequent tissue property value to determine a delta value between the initial tissue property value and the subsequent tissue property value;
      determine whether the delta value reaches a threshold value; and
      provide an output in response to determining that the delta value reaches the threshold value.

2. The surgical system of claim 1, wherein the generator is configured to control the supply of the ultrasonic energy to heat the tissue grasped between the first jaw member and the second jaw member to a predetermined temperature for a period of time until the tissue grasped between the first jaw member and the second jaw member is sealed.

3. The surgical system of claim 1, wherein the initial and subsequent tissue property values are tissue impedance values and wherein the delta value is an impedance difference value between the initial and subsequent tissue impedance values.

4. The surgical system of claim 3, wherein the output is a determination of desiccation or coagulation of the tissue grasped between the first jaw member and the second jaw member based on the delta.

5. The surgical system of claim 3, wherein the output is an audio tone when the delta value reaches the threshold value.

6. The surgical instrument of claim 1, wherein the return electrode is a return pad.

7. A surgical instrument, comprising:
   an ultrasonic transducer;
   an ultrasonic waveguide coupled with the ultrasonic transducer;
   a conductor;
   an end effector assembly including a first jaw member having an electrically-conductive tissue-contacting surface connected to the conductor and a second jaw member positioned opposite the first jaw member, wherein the first and second jaw members are configured to grasp tissue therebetween, and wherein one of the first jaw member or the second jaw member includes a blade acoustically coupled to the ultrasonic waveguide to receive ultrasonic energy produced by the transducer and transmitted along the ultrasonic waveguide; and
   a controller configured to:
      apply an initial current pulse to the grasped tissue through the conductor and measure an initial current feedback signal in response to the initial current pulse;
      estimate an initial tissue property value of the grasped tissue based on the initial current feedback signal;
      drive the ultrasonic transducer to produce the ultrasonic energy transmitted from the ultrasonic transducer along the ultrasonic waveguide to the blade;
      apply a subsequent current pulse through the conductor and measure a subsequent current feedback signal in response to the subsequent current pulse;
      estimate a subsequent tissue property value based on the subsequent current feedback signal;
      compare the initial tissue property value with the subsequent tissue property value to determine a delta value between the initial tissue property value and the subsequent tissue property value;
      determine whether the delta value reaches a threshold value; and
      provide an output in response to determining that the delta value reaches the threshold value.

8. The surgical instrument of claim 7, wherein the controller is configured to drive the ultrasonic transducer such that the blade heats the grasped tissue to a predetermined temperature, and maintains the temperature for a period of time, and wherein the end effector assembly applies clamping force to compress the grasped tissue until the grasped tissue is sealed.

9. The surgical instrument of claim 7, wherein the electrically-conductive tissue-contacting surface of the first jaw member is adapted to apply the initial and subsequent current pulses to the grasped tissue.

10. The surgical instrument of claim 7, wherein the controller sequentially applies the initial current pulse, drives the ultrasonic transducer, and applies the subsequent current pulse.

11. The surgical instrument of claim 7, wherein the controller applies the current pulses and drives the ultrasonic transducer at different times by periodically switching between applying current and driving the ultrasonic transducer.

12. A surgical system, comprising:
an ultrasonic device configured to receive ultrasonic energy for treating tissue;
a return electrode remote from the ultrasonic device; and
a generator coupled to the ultrasonic device and the return electrode, the generator configured to:
control supply of the ultrasonic energy to the ultrasonic device;
control supply of first and second energy pulses to the ultrasonic device;
measure first and second current feedback signals at the return electrode in response to the first and second energy pulses, respectively;
estimate first and second tissue property values based on the first and second current feedback signals, respectively;
compare the first and second tissue property values to determine a delta value between the first and second tissue property values;
determine whether the delta value reaches a threshold value; and
determine that a tissue treatment has been completed in response to determining that the delta value reaches the threshold value.

13. The surgical system according to claim 12, wherein the return electrode is a return pad.

14. The surgical system according to claim 12, wherein the ultrasonic instrument includes first and second jaw members configured to grasp tissue, one of the first jaw member or the second jaw member configured to apply the ultrasonic energy to the grasped tissue.

15. The surgical system according to claim 14, wherein another of the first jaw member or the second jaw member is configured to apply the first and second energy pulses to the grasped tissue.

16. The surgical system according to claim 12, wherein the first and second tissue property values are first and second tissue impedance values, respectively.

17. The surgical system according to claim 12, wherein the determination that tissue treatment has been completed is a determination that desiccation or coagulation of tissue has been completed.

* * * * *